United States Patent [19]

Takeuchi

[11] Patent Number: 4,939,468
[45] Date of Patent: Jul. 3, 1990

[54] CAPACITIVE FLUID SENSOR

[75] Inventor: Kiyoshi Takeuchi, Yokohama, Japan

[73] Assignee: Nissan Motor Co., Ltd., Yokohama, Japan

[21] Appl. No.: 302,881

[22] Filed: Jan. 30, 1989

[30] Foreign Application Priority Data

Jan. 30, 1988 [JP] Japan .................................. 63-20900

[51] Int. Cl.⁵ ............................................ G01N 27/22
[52] U.S. Cl. .................... 324/690; 324/686; 324/663
[58] Field of Search ............ 73/861.28, 861.89, 861.92; 324/61 P, 65 P, 446, 447, 448, 449, 690, 686, 667, 663

[56] References Cited

U.S. PATENT DOCUMENTS

| | | | |
|---|---|---|---|
| 1,483,225 | 2/1924 | Hammett | 73/861.92 |
| 1,511,765 | 10/1924 | Latham | 73/861.92 |
| 1,585,255 | 5/1926 | McFadden | 73/861.92 |
| 3,025,464 | 3/1962 | Bond | 324/61 P |
| 3,133,437 | 5/1964 | Remke | 324/61 P |
| 3,314,005 | 4/1967 | Whitener | 324/61 P |
| 4,774,680 | 9/1988 | Agar | 324/61 P |
| 4,809,129 | 2/1989 | Hansen | 324/61 P |

FOREIGN PATENT DOCUMENTS

| | | | |
|---|---|---|---|
| 0733732 | 5/1966 | Canada | 324/61 P |
| 0743666 | 9/1966 | Canada | 324/61 P |

Primary Examiner—Reinhard J. Eisenzopf
Assistant Examiner—Jose M. Solis
Attorney, Agent, or Firm—Foley & Lardner, Schwartz, Jeffery, Schwaab, Mack, Blumenthal & Evans

[57] ABSTRACT

To increase the sealing effect with increasing fluid pressure in a capacitive fluid sensor for sensing a dielectric constant of fluid, the sensor comprises a sensor housing, a fluid outlet pipe connected midway in the sensor housing, an internal electrode, a first cylindrical insulating internal electrode support member disposed within the sensor housing between the fluid outlet pipe and a sensor housing end, and a sealing member disposed between the first cylindrical support member and sensor housing end. It is preferable to dispose a second flat insulating internal electrode support member formed with a central annular portion and plural arms extending from the annular portion so as to be fitted to a swollen-out portion of the sensor housing to reduce fluid resistance.

12 Claims, 11 Drawing Sheets

CAPACITIVE FLUID SENSOR

BACKGROUND OF THE INVENTION

1. Field of the Invention

The present invention relates to a capacitive fluid sensor and more specifically to a fluid sensor for sensing the dielectric constant of fluid flowing through a sensor housing. By sensing a change in capacitance influenced by the dielectric constant, it is possible to ascertain the concentration or mixture ratio of two substances, for instance.

2. Descritpion of the Prior Art

Recently, fuel mixtures of petroleum fuel (gasoline or petrol) and alcohol fuel (methanol or methyl alcohol) has been used to drive engines for the purpose of reducing the dependency of the vehicles upon petroleum fuel. In the mixed fuel, it is necessary to detect a mixture ratio of petroleum fuel to alcohol fuel in order to regulate the quantity of fuel to be supplied to an engine, ignition timing, etc. In other words, an optimum engine output is required, even when the mixture ratio changes.

As sensors for detecting mixture ratios of petroleum and alcohols fuels, a capacitive fluid sensor for detecting dielectric constants of fluid flowing therethrough has been known, because the dielectric constant of petroleum fuel differs from that of alcohol. In the prior-art capacitive fluid sensor, however, there exists a problem in that fuel tends to leak from the sensor housing through an electric connector portion, when the pressure of fuel flowing through the fluid sensor housing increases.

The structure of the prior-art capacitive fluid sensor will be described in more detail hereinbelow for comparison purposes with reference to the detached drawings under DETAILED DESCRIPTION OF THE PREFERRED EMBODIMENTS.

SUMMARY OF THE INVENTION

With these problems in mind, therefore, it is the primary object of the present invention to provide a capacitive fluid sensor which can securely prevent fluid from leaking from the sensor housing through an electric connector portion.

To achieve the above-mentioned object, a capacitive fluid sensor, according to the present invention, for sensing a dielectric constant of fluid comprises: (a) a sensor housing within which fluid to be sensed flows from a first housing end toward a second housing end, the sensor housing constituting an external electrode; (b) a fluid outlet pipe connected to the sensor housing midway between the first and second housing ends; (c) an internal electrode; (d) a first insulating support member, disposed within the sensor housing and between the fluid outlet pipe and the second housing end, for supporting the internal electrode within the sensor housing and closing the second housing end; and (e) a sealing member, disposed between the first insulating support member and the sensor housing near the second housing end, for sealing the fluid to be sensed in the sensor housing in such a way that sealing force increases with increasing fluid pressure.

In the capacitive fluid sensor of the present invention, since the sealing member is increasingly compressed between the first insulating support member and an end of the sensor housing with increasing fluid pressure within the sensor housing, it is possible to effectively prevent fluid to be sensed from leaking from the sensor housing.

Further, it is preferable to dispose a second flat insulating internal electrode support member formed with a central annular portion and plural arms extending from the annular portion so as to be fitted to a swollen-out portion of the sensor housing to reduce fluid resistance.

BRIEF DESCRIPTION OF THE DRAWINGS

FIG. 14(b) is a front view showing a cross-shaped internal electrode support member of the second embodiment;

FIG. 14(c) is a side view showing the internal electrode of the second embodiment;

FIG. 15(b) is a cross-sectional view showing the cross-shaped internal electrode support member of the second embodiment;

FIG. 15(c) is a cross-sectional view showing the internal electrode of the second embodiment;

DETAILED DESCRIPTION OF THE PREFERRED EMBODIMENTS

To facilitate understanding of the present invention, a brief reference will be made to a prior-art capacitive fluid sensor with reference to the attached drawings.

Figure 1:
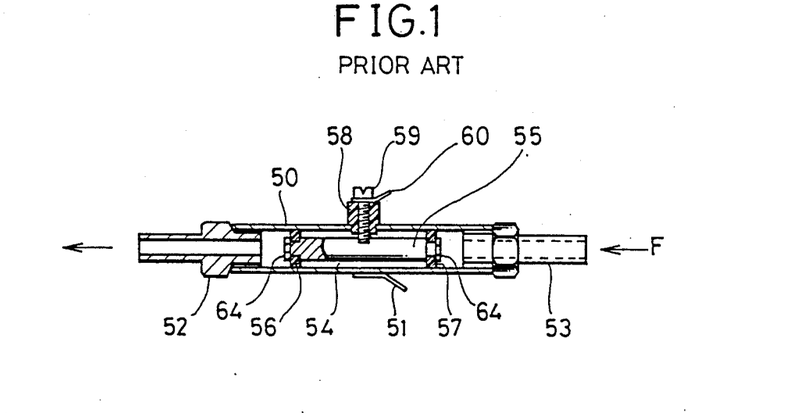
FIG. 1 is a partial longitudinal cross-sectional view showing a prior-art capacitive fluid sensor.
Figure 2A:
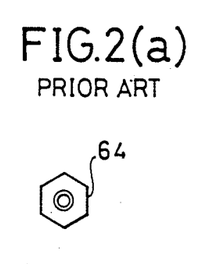
FIG. 2(a) is a front view showing a nut for fixing an internal electrode to an internal electrode support member of the prior-art sensor shown in the FIG. 1.

FIGS. 1, 2(a), (b), (c) and 3(a), (b), (c) show an example of prior-art fluid sensors of the electric capacitance type. In FIG. 1, the sensor comprises a cylindrical metal sensor housing 50 (i.e. a first external electrode), an external electrode (grounded) terminal 51 fixed to the housing 50, two hose connectors 52 and 53 screwed into both ends of the cylindrical sensor housing 50, an internal electrode 55 (i.e. a second internal electrode) supported at the center of the sensor housing 50, two insulating internal electrode support members 56 and 57, a bolt 59 screwed into the internal electrode 55 via an insulating bushing 58 in the radial direction of the sensor housing 50, and an internal electrode terminal 60 fixed to the bolt 59 or the internal electrode 55.

Therefore, when two hoses (not shown) are connected to the two hose connectors 52 and 53, fluid F can be passed through a space 54 formed between the inner circumferential surface of the sensor housing 50 and the outer circumferential surface of the internal electrode 55.

Figure 2B:
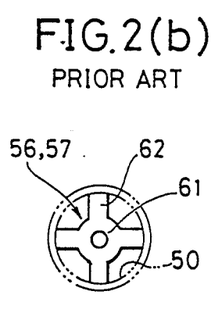
FIG. 2(b) is a front view showing a cross-shaped internal electrode support member of the prior-art sensor.
Figure 2C:
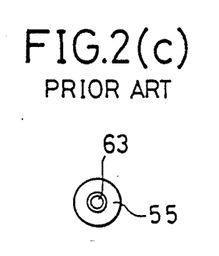
FIG. 2(c) is a side view showing the internal electrode of the prior-art sensor.
Figure 3A:
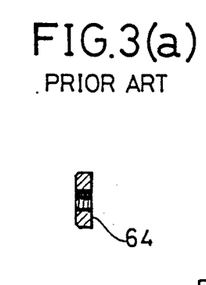
FIG. 3(a) is a cross-sectional view showing the internal electrode fixing nut.
Figure 3B:
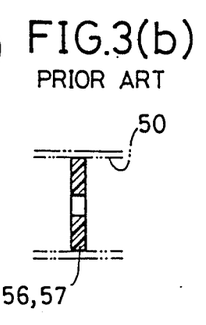
FIG. 3(b) is a cross-sectional view showing the cross-shaped internal electrode support member.
Figure 3C:
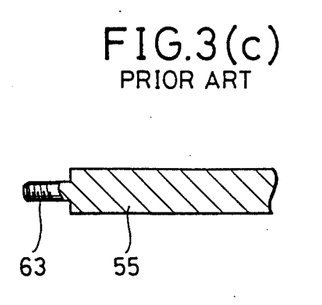
FIG. 3(c) is a cross-sectional view showing the internal electrode.

In more detail with reference to FIGS. 2 and 3, the two insulating internal electrode support numbers 56 and 57 are formed as shown in FIG. 2(b), in which four cross-shaped arm portions 62 extend from a central annular portion 61. The electrode support members 56 and 57 are fitted to male thread portions 63 formed on both sides of the internal electrode 55 and fixed by nuts 64, respectively. In assembly, two support members 56 and 57 are first fixed to the internal electrode 55 at both the ends thereof with nuts 64, and thereafter the internal electrode 55 is inserted into the cylindrical sensor housing 50 as shown in FIG. 1.

Figures 4, 5:
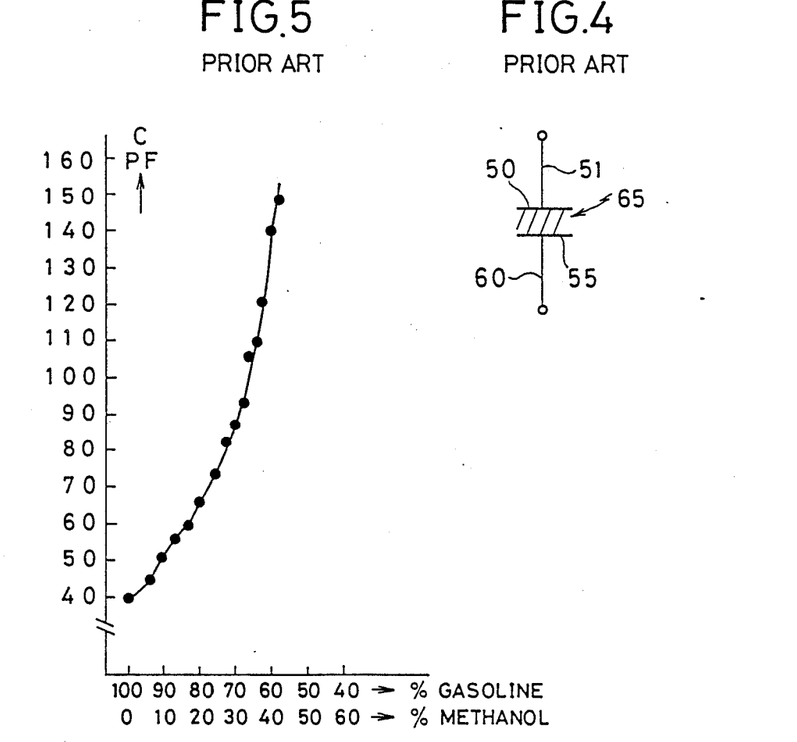
FIG. 4 is an equivalent circuit of the prior-art capacitive fluid sensor shown in FIG. 1.
FIG. 5 is a graphical representation showing the relationship between fuel mixture ratio and electrostatic capacitance of the prior-art sensor shown in FIG. 1.

Therefore, a capacitor 65 as shown in FIG. 4 can be formed, in which the cylindrical sensor housing 50 is a first electrode to which the grounded terminal 51 is connected and the internal electrode 55 is a second electrode to which the internal electrode terminal 60 is connected when fluid F is passed through the sensor housing 50, as a dielectric substance.

In general, the electrostatic capacitance C of the capacitor 65 can be expressed as:

$$C = (A/t) \cdot (\epsilon/\epsilon 0) \cdot \epsilon 0$$

where A denotes the electrode area (cm$^2$); t denotes the distance between two electrodes (cm); $\epsilon$ denotes the dielectric constant (F/cm) of the dielectric substance; $\epsilon 0$ denotes the dielectric constant in a vacuum ($8.854 \times 10^{-4}$ F/cm); and $\epsilon/\epsilon 0$ denotes a relative dielectric constant of the dielectric substance.

Therefore, where A and t are constant, since the electrostatic capacitance C (F) varies in proportion to the relative dielectric constant $\epsilon/\epsilon 0$ of the dielectric substance, it is possible to sense relative dielectric constant of the dielectric substance (i.e. fuel F) by detecting the electrostatic capacitance C. For instance, since the relative dielectric constant of gasoline (petrol) is about 1.95 and that of methanol (methyl alcohol) is about 32.4, the relative dielectric constant of mixed fuel changes according to the mixture ratio. In other words, it is possible to detect the mixture ratio by sensing the electrostatic capacitance C formed within the capacitive fluid sensor.

Figure 6:
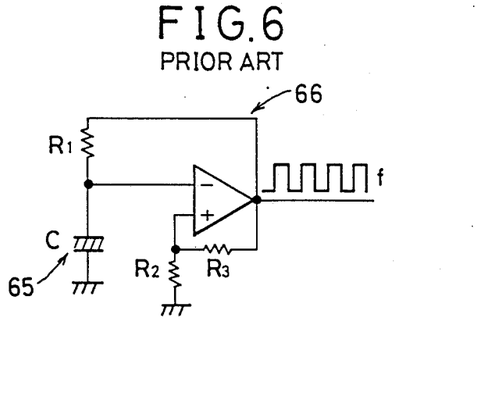
FIG. 6 is an example of oscillator circuits for detecting the capacitance detected by the sensor.

FIG. 5 shows an example of change in the electrostatic capacitance C according to the mixture ratio of the gasoline and methanol. Inpractice, the change in the electrostatic constant C can be detected in the form of the change in oscillation frequency f. FIG. 6 shows an example of an oscillator circuit 66 in which the frequency f of the output signal can be determined by the circuit constants including resistors R1, R2 and R3 and the capacitance C. In other words, it is possible to ascertain the mixture ratio represented by capacitance C by measuring the frequency f of the output signal of the oscillator circuit 66.

In the prior-art capacitive fluid sensor as described above, however, since the inner space of the cylindrical sensor housing 50 is closed by a bushing 58 simply fixed to the sensor housing by the bolt 59, there exists a problem in that fuel flowing though the sensor housing leaks from the electric connection portion when fluid pressure increases, because the bolt 59 and the bushing 58 are urged in the outward direction away from the sensor housing 50 by the fluid pressure within the sensor housing 50.

In view of the above description, reference is now made to a first embodiment of the capacitive fluid sensor according to the present invention. The feature of the fluid sensor according to the present invention is to provide a novel sensor structure such that a cylindrical internal electrode support member is used in common as an electric internal electrode connector and further as a sealing O-ring sandwiched between the cylindrical internal electrode support member and the sensor housing in such a way that the sealing force increases with increasing fluid pressure.

Figures 7A, 7B:
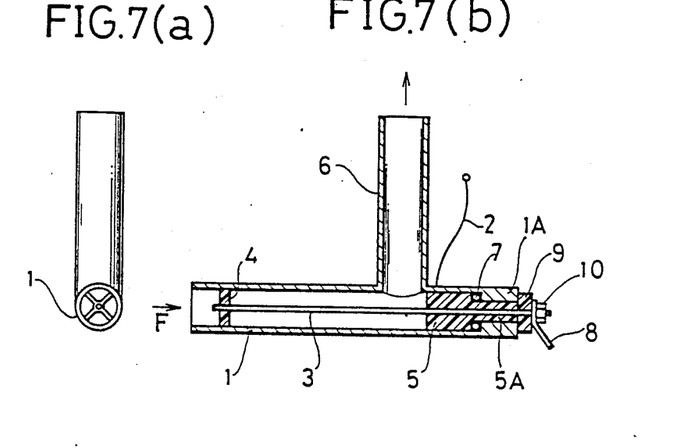
FIG. 7(a) is a side view showing a first embodiment of a capacitive fluid sensor according to the present invention.
FIG. 7(b) is a longitudinal cross-sectional view showing the first embodiment of the capacitive fluid sensor.

FIGS. 7(a) and (b) show a first embodiment of the present invention. This fluid sensor comprises a cylindrical metal sensor housing 1 (i.e. a first external electrode), an external electrode (grounded) wire 2 fixed to the sensor housing 1, an internal electrode 3 (i.e. a second internal electrode) supported at the center of the sensor housing, a cross-shaped flat insulating internal electrode support member 4 (similar to the prior-art one), a plug-shaped cylindrical insulating internal electrode support member 5, a fuel outlet pipe 6 fixed to the housing 1 near an inner end of the plug-shaped cylindrical support member 5, an O-ring sealing member 7 disposed between the plug-shaped cylindrical support member 5 and the sensor housing 1, an internal electrode terminal 8 fixed between an insulating bushing 9 and a nut 10. In other words, the plug-shaped support member 5 is disposed within the sensor housing 1 and between the fluid outlet pipe 6 and an outer end of the sensor housing 1.

The left side of the cylindrical sensor housing 1 is used in common as a hose connector and further the upper side of the fuel outlet pipe 6 is used in common as a hose connector, in FIG. 7(b). The internal electrode 3 is screwed into the cross-shaped flat support member 4. However, if the rigidity of the internal electrode 3 is high enough, the cross-shaped internal electrode support member 4 can be omitted.

The plug-shaped cylindrical internal electrode support member 5 is formed with a shoulder portion and a small-diameter portion (projection end) 5A so as to be passed through a small inner diameter portion 1A of the sensor housing 1, and the O-ring is disposed between the shoulder portion of the plug-shaped support member 5 and a shoulder portion of the small inner diameter portion 1A of the housing 1. Further, the internal electrode 3 is passed through the plug-shaped cylindrical support member 5 into the sensor housing 1, and fixed by the nut 10 via the insulating bushing 9, and further the internal electrode terminal 8 is fixed between the bushing 9 and the nut 10.

In the fluid sensor as described above, two fuel hoses (not shown) are connected to the outside ends of the sensor housing 1 and the outlet pipe 6, respectively and mixed fuel F is passed in the arrow directions in FIG. 7(b, in order to measure the mixture ratio of gasoline and methanol. In general, the pressure of the mixed fuel increases to about 10 kg/cm$^2$. In the fluid sensor structure of the present invention, however, since the O-ring sealing member is disposed between the shoulder portion of the plug-shaped cylindrical support member 5 and the shoulder portion of the small inner diameter portion 1A of the sensor housing 1, the inner fluid pressure applied to the plug-shaped support member 5 is received by the small inner diameter portion 1A via the O-ring 7. That is, since the shape of the O-ring 7 is increasingly deformed or compressed as fluid pressure increases, it is possible to further increase the sealing force between the plug-shaped internal electrode support member 5 and the sensor housing 1, so that fuel leakage function is improved more effectively and stably.

Figure 8:
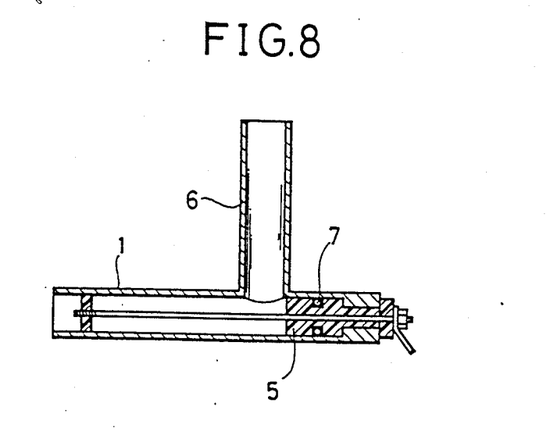
FIG. 8 is a longitudinal cross-sectional view showing a first modification of the first embodiment.

FIG. 8 shows a first modification of the first embodiment, in which the O-ring 7 is disposed midway at the large diameter portion of the plug-shaped cylindrical support member 5 to seal the fluid between the plug-shaped cylindrical support member 5 and the inner circumferential surface of the sensor housing 1.

Figure 9A:
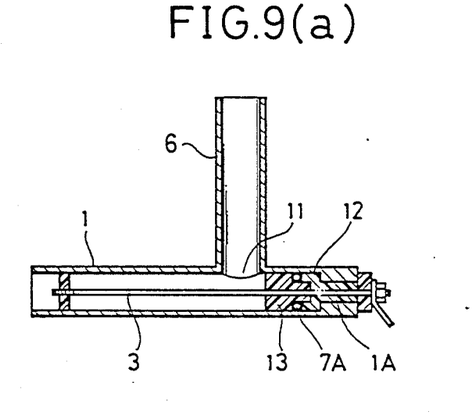
FIG. 9(a) is a longitudinal cross-sectional view showing a second modification of the first embodiment.
Figure 9B:
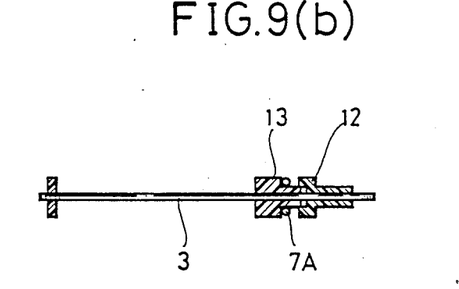
FIG. 9(b) is a longitudinal cross-sectional view showing only an internal electrodes assembly of the sensor shown in FIG. 9(a)

FIGS. 9(a) and 9(b) show a second modification of the first embodiment, in which the plug-shape support member 5 is divided into a first cylindrical insulating support member 13 formed with a shoulder portion and a projection end and a second cylindrical insulating support member 12 formed with a shoulder portion and a recessed end engageable with the projection end of the first cylindrical support member 13. Further, the O-ring sealing member 7A is disposed between the two shoulder portions of the two cylindrical insulating support members 13 and 12. Further, the outer diameter of the O-ring 7A is set a little smaller than the inner diameter of the housing 1.

To joint the fluid outlet pipe 6 to the sensor housing 1, a hole is first formed in the radial direction of the housing 1 and then the outlet pipe 6 is welded or soldered to the housing 1. In this case, there exists a problem in that burr or risen soldering portion are usually formed at the joint portion, so that the O-ring is often damaged when inserted into the inner space of the cylindrical sensor housing 1.

To overcome the above-mentioned problem, the internal electrode 3 is supported by only the second cylindrical support member 12. On the other hand, the first cylindrical support member 13 is axially slidably fitted to the internal electrode 3 in such a way that the O-ring 7A can be disposed between the two shoulder portions of the two first and second members 12 and 13. In this modification, since the O-ring is compressed by the support member 13 and the outer diameter thereof increases when fluid pressure increases, it is possible to seal the fluid within the sensor housing 1 as effectively as in the first embodiment shown in FIGS. 7(a) and (b).

Figure 10:
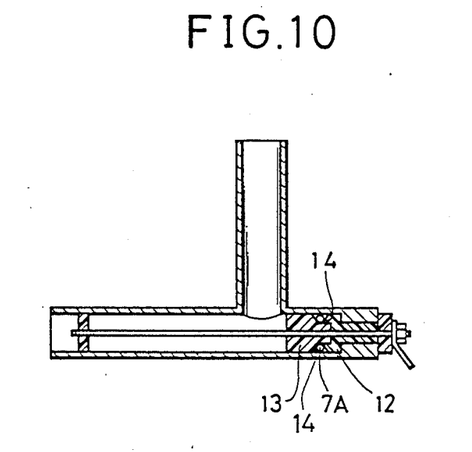
FIG. 10 is a longitudinal cross-sectional view showing a third modification of the first embodiment.

FIG. shows a third modification of the first embodiment, which improves the second modification shown in FIGS. 9(a) and (b). That is, the surfaces of the two shoulder portions 14 of the two support members 12 and 13 with which the O-ring 7A is in contact are chamfered or tapered. Therefore, when fluid pressure increases, it is possible to more effectively compress the sandwiched O-ring sealing member 7A in the radially outward direction, thus improving the sealing function.

Figure 11:
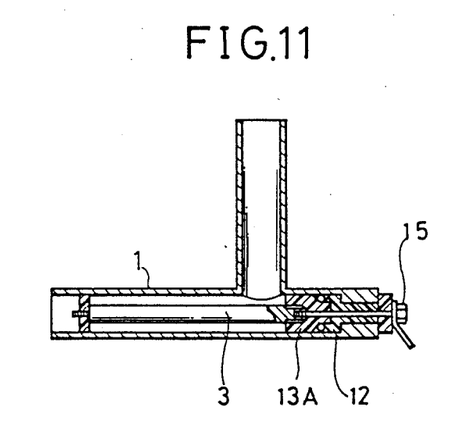
FIG. 11 is a longitudinal cross-sectional view showing a fourth modification of the first embodiment.

FIG. 11 shows a fourth modification of the first embodiment, in which the diameter of the internal electrode 3 is increased; a male threaded end therefore is screwed into a female threaded bore portion of the first cylindrical support member 13A; and the internal electrode 3 is fixed to the sensor housing 1 by a bolt 15. In this modification, it is also possible to form the internal electrode 3 and the first cylindrical support member 13A integral with each other by a metal material without connecting these two members via screw threads.

Figure 12A:
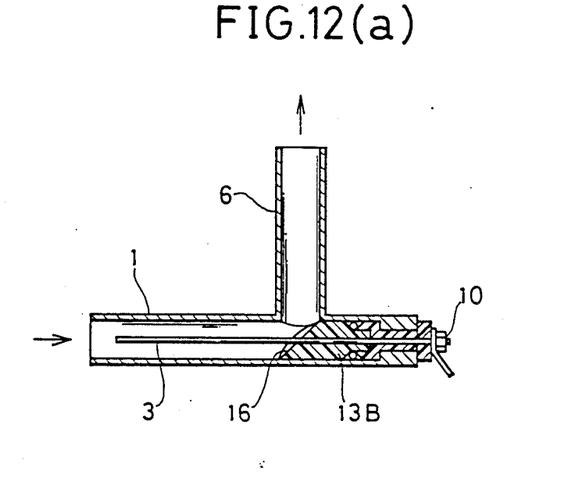
FIG. 12(a) is a longitudinal cross-sectional view showing a fifth modification of the first embodiment.
Figure 12B:
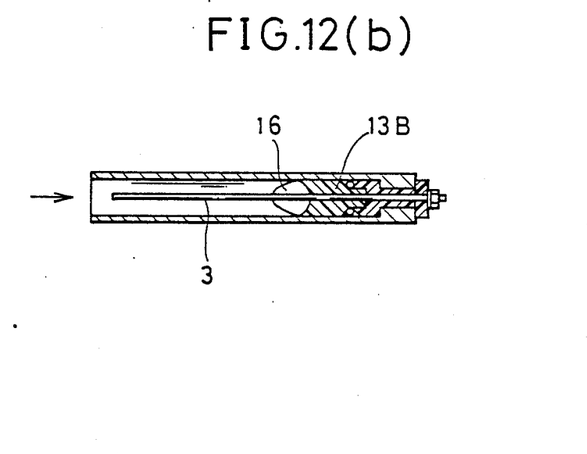
FIG. 12(b) is a similar cross-sectional vew, when seen from above, showing the fifth modification of the first embodiment.

FIGS. 12(a) and (b) shows a fifth modification of the first embodiment, in which the inner surface (against which fluid flows) of the first cylindrical support member 13B is tapered so as to provide an inclinaton surface 16, to more smoothly change fluid flow direction from the sensor housing 1 toward the outlet pipe 6. Further, it is more preferable to form this inclination surface 16 into a concave surface to smoothly pass the fluid from the sensor housing 1 toward the outlet pipe 6 in a stationary flow state so that the flow resistance can be reduced without producing vortexes or bubbles. In addition, since the first cylindrical support member 13B can cover the inner circummferential surfaces of the sensor housing 1 (i.e. external electrode) and the internal electrode 3 more broadly as compared with the other modifications, it is possible to prevent the electric resistance of the electrodes 1 and 3 from being reduced due to adherence of foreign substances, thus providing more stable capacitor characteristics. Furthermore, when the concave inclination surface is engaged with another convex inclination surface of a fixing jig, it is possible to prevent the first support member 13B from being rotated together with the nut 10 during the assembly process.

Figure 13:
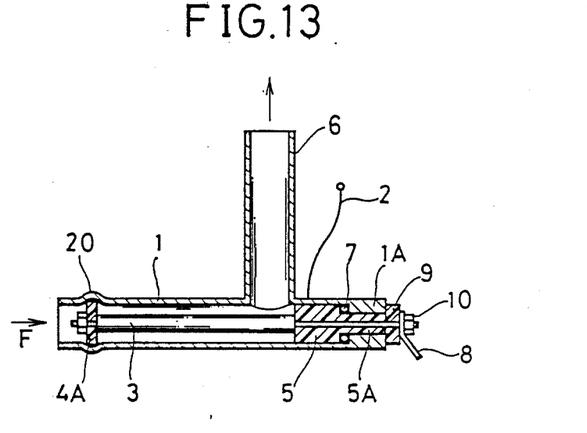
FIG. 13 is a longitudinal cross-sectional view showing a second embodiment of the capacitive fluid sensor according to the present invention.

FIG. 13 shows a second embodiment of the capacitive fluid sensor according to the present invention, in which the second flat internal electrode support member 4A disposed on the fuel inlet side is improved to reduce fluid resistance of the fuel F flowing through the sensor housing 1.

Figure 14A:
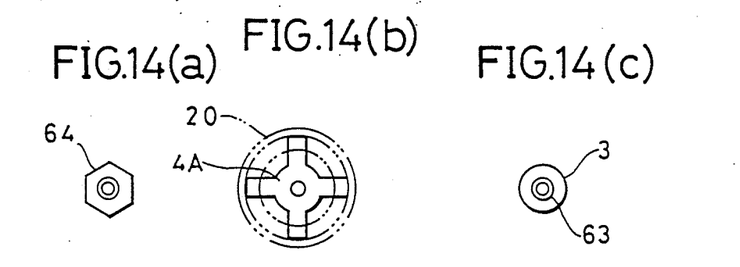
FIG. 14(a) is a front view showing a nut for fixing an internal electrode to an internal electrode support member of the second embodiment of the capacitive fluid sensor shown in FIG. 13.
Figure 15A:
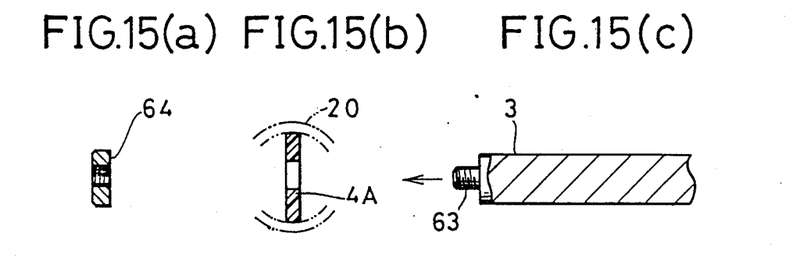
FIG. 15(a) is a cross-sectional view showing the internal electrode fixing nut of the second embodiment.

In this second embodiment, the cylindrical sensor housing 1 is formed with a swollen-out portion 20 near the fuel inlet end side of the housing 1 by bulge processing, so that the cross-shaped internal electrode support member 4A can be fitted to this swollen-out portion 20. The shape of this second support member 4A is substantially the same as that of the prior-art member 56 or 57 shown in FIG. 2(b) except four cross-shaped arms longer than those of the prior-art one, as shown in FIGS. 14(b) and 15(b) are provided. That is, the support member 4A is formed with four cross-shaped arms extending from a central annular portion, fitted to a male thread portion 63 of the internal electrode 3, and then fixed to the internal electrode 3 by a nut 64 as shown in FIGS. 14(a) and 15(a).

In this second embodiment, it is possible to prevent the fluid path area from being reduced at the position where the internal electrode support member 4A is attached by increasing the inner diameter of the sensor housing 1, thus reducing the fluid resistance of the sensor.

Figure 16:
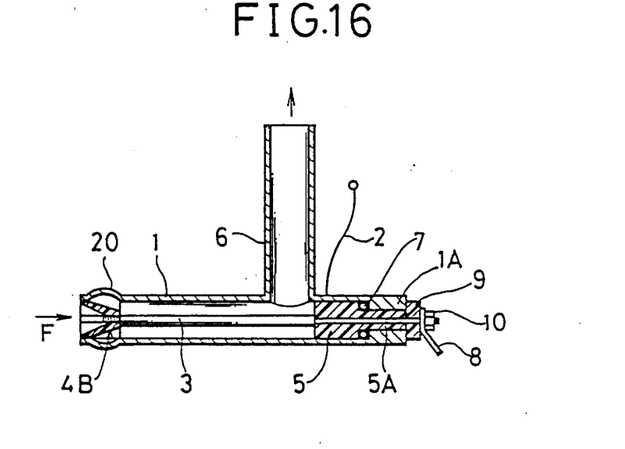
FIG. 16 is a longitudinal cross-sectional view showing a first modification of the second embodiment.
Figure 17A:
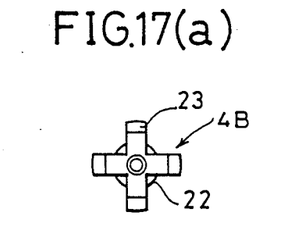
FIG. 17(a) is a front view showing a cross-shaped internal electrode support member of the first modification of the second embodiment.
Figure 17B:
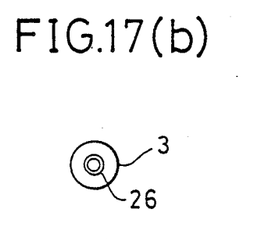
FIG. 17(b) is a side view showing the internal electrode of the first modification of the second embodiment.
Figure 18A:
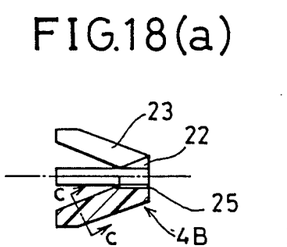
FIG. 18(a) is a cross-sectional view showing a cross-shaped internal electrode support member of the first modification of the second embodiment.
Figure 18B:
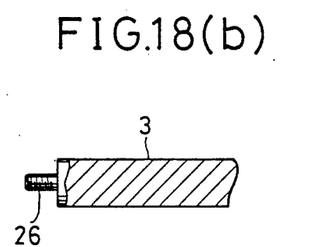
FIG. 18(b) is a cross-sectional view showing an internal electrode of the first modification of the second embodiment.

FIG. 16 shows a first modification of the second embodiment, by which the internal electrodes 3 screwed into the second support member 4B can more easily be inserted into the sensor housing 1. In more detail, the second internal electrode support member 4B is formed with four cross-shaped arms 23 extending toward the outside of the housing 1, at an inclination angle with respect to the axial direction of the housing 1, from the central annular portion 22 as shown in FIGS. 17(a) and 18(a). Further, the threaded portion 26 (shown in FIGS. 17(b) and 18(b)) of the internal electrode 3 is located near the swollen-out portion 20 of the housing 1 so that the radially outermost ends of the inclined arms 23 can be brought into contact with the inner circumferential surface of the housing 1 outward away from the swollen-out portion 20.

Figure 18C:
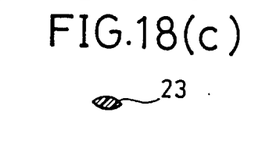
FIG. 18(c) is a cross-sectional view showing a fin-shaped arm of the cross-shaped internal electrode support member shown in FIG. 18(a)

In this modification, since the outer diameter of the second support member 4B is roughly the same as the inner diameter of the housing 1, it is possible to more easily assemble the internal electrode 3 into the sensor housing 1. Further, when the cross-sectional shape of each arm 23 is formed into a fin shape as depicted in FIG. 18(c), it is possible to further reduce the fluid resistance while increasing the fluid path area. The second support member 4B can be fixed to the internal electrode 3 by screwing the male thread portion 26 of the internal electrode 3 into the female thread portion 25 of the support member 4B as shown in FIGS. 17(a) and (b) and 18(a) and (b).

Figure 19A:
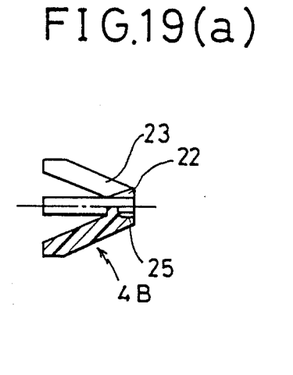
FIG. 19(a) is a cross-sectional view showing a cross-shaped internal electrode support member of the second modification of the second embodiment.
Figure 19B:
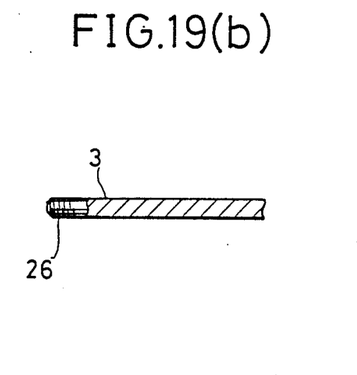
FIG. 19(b) is a cross-sectional view showing an internal electrode of the second modification of the second embodiment.

FIGS. 19(a) and (b) show a second modification of the second embodiment of the fluid sensor, in which the diameter of the internal electrode 3 is reduced down to the outer diameter of the male thread portion 26 thereof to further reduce the fluid resistance of the sensor.

Figure 20:
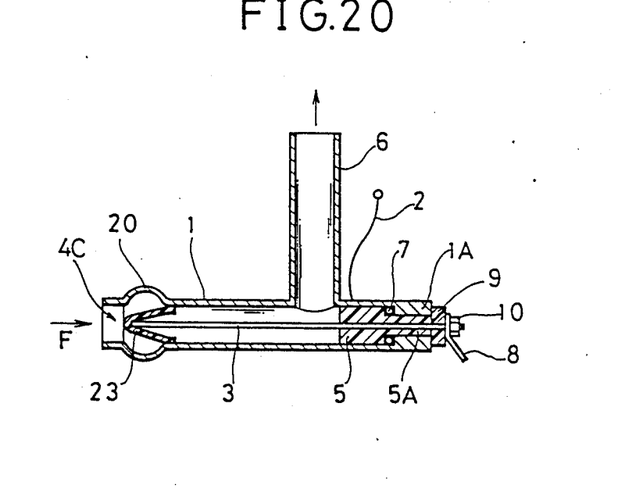
FIG. 20 is a longitudinal cross-sectional view showing a third modification of the second embodiment.

FIG. 20 shows a third modification of the second embodiment. In this modification, the second internal electrode support member 4C is formed with four cross-shaped arms 23 extending toward the inside of the housing 1 inward away from the swollen-out portion 20, at an inclination angle with respect to the axial direction of the housing 1, from the central annular portion. In this modification, it is possible to more accurately dispose the internal electrode 3 at the center of the sensor housing 1, as compared with the first and second modifications, because the second internal electrode support member 4C can be brought into contact with the more inside inner circumferential surface of the housing 1.

Figure 21A:
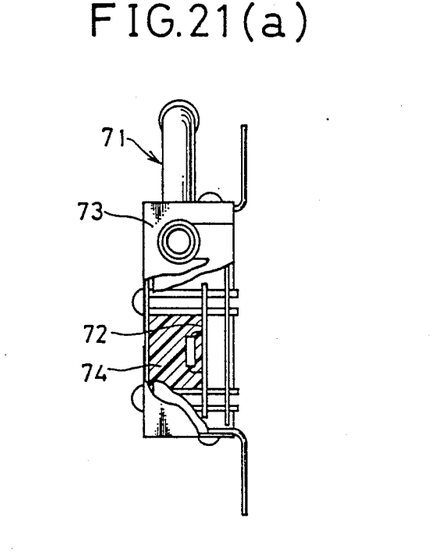
FIG. 21(a) is a partially broken side view showing a detector apparatus in which the capacitive fluid sensor shown in FIG. 10 (the third modification of the first embodiment) and an oscillator circuit are incorporated.
Figure 21B:
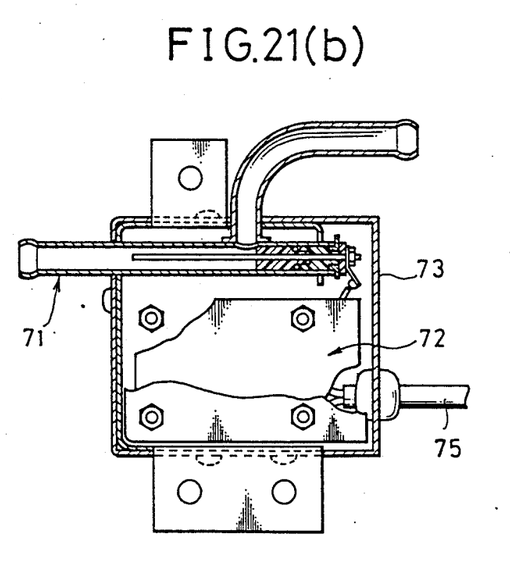
FIG. 21(b) is a partially broken front view showing the same detector apparatuus shown in FIG. 21(a)

FIGS. 21(a) and (b) shows a exemplary arrangement of an alcohol concentration detector for detecting a mixture ratio of gasoline to alcohol, to which the capacitive fluid sensor 71 (as shown in FIG. 10) of the present invention is incorporated in a circuit section 72 within a casing 73. In the drawings, the circuit section 72 is bonded within the casing 73 and is connected to an external connection cable 75.

Figure 22:
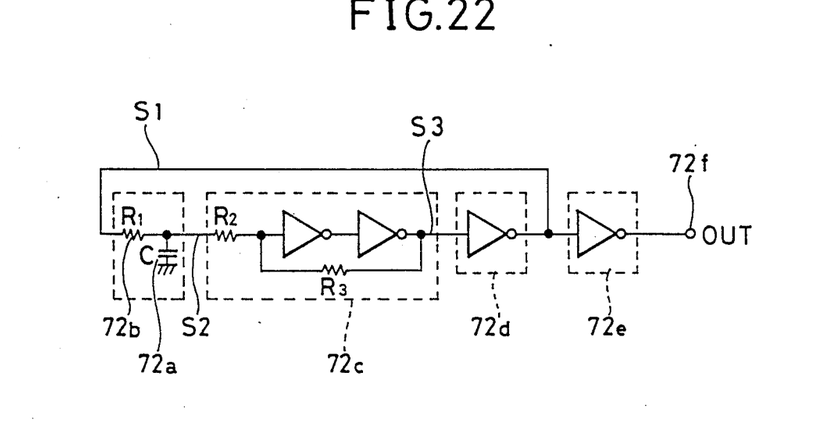
FIG. 22 is a block diagram showing an oscillator circuit of the electrostatic capacitive fluid sensor.
Figure 23:
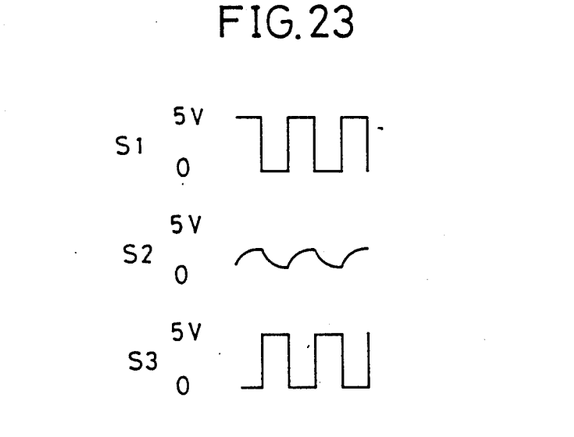
FIG. 23 is a waveform timing chart for assitance in explaining the oscillator circuit shown in FIG. 22.

FIG. 22 shows an example of the circuit section 72, which comprises an integration circuit composed of a resistor R1 (72b) and a capacitor C (72a) formed between the sensor external electrode (sensor housing) 1 and the sensor internal electrode 3, a hysteresis comparator 72C for generating a high-voltage level signal when an input signal voltage level exceeds a predetermined level, an inverter 72d, and a bufer amplifier 72e. Further, FIG. 23 is a signal timing chart of an input signal S1 to the integration circuit, an output signal S2 from the integration circuit, and an output signal S3 from the comparator 72C. Since the time constant of the integration circuit can be varied when the capacitance C of the fluid sensor 72a changes, it is possible to output a pulse signal whose frequency varies according to the capacitance C, from an output terminal 72f. That is, the alcohol concentraton of mixed fuel can be detected by measuring the frequency of the output signal generated by the detector circuit section 72.

The capacitive fluid sensor according to the present invention has been explained as a mixed fuel concentration sensor by way of example. Without being limited, however, the fluid sensor of the present invention can be applied to various sensors for measuring physical characteristics dependent upon the dielectric constant of fluids.

What is claimed is:
1. A capacitive fluid sensor for sensing a dielectric constant of fluid, said capacitive fluid sensor comprising:
 (a) a sensor housing within which fluid to be sensed flows from a first housing end toward a second housing end, said sensor housing forming an external electrode;
 (b) a fluid outlet pipe connected to said sensor housing between said first and second housing ends;
 (c) an internal electrode;
 (d) a first insulating support member, disposed within said sensor housing between said fluid outlet pipe and said second housing end, supporting said inter- nal electrode within said sensor housing and closing said second housing end; and (e) a sealing member, disposed between said first insulating support member and said sensor housing near said second housing end, sealing fluid to be sensed in said sensor housing such that sealing force increases fluid pressure.

2. The capacitive fluid sensor of claim 1, wherein said first insulating support member includes:

(a) a first cylindrical insulating support member formed with a first shoulder portion and a projection end; and (b) a second cylindrical insulating support member formed with a second shoulder portion and a recessed end engageable with said projection end of said first cylindrical support member, and wherein said sealing member includes an O-ring disposed between said first and second shoulder portions.

3. The capacitive fluid sensor of claim 2, wherein shoulder portion surfaces of said first and second cylindrical insulating support members are formed into tapered surfaces so that said sealing member moves radially outwards when fluid pressure increases.

4. The capacitive fluid sensor of claim 2, wherein an inward end surface of said first cylindrical insulating support member is formed into an inclined plane, at a position where said fluid outlet pipe is connected to said sensor housing, to smoothly change fluid flow direction from said sensor housing toward said fluid outlet pipe.

5. The capacitive fluid sensor of claim 4, wherein said inclined plane is formed into a concave surface.

6. The capacitive fluid sensor of claim 1, which further comprises a second insulating support member supporting said internal electrode within said sensor housing at said first housing end.

7. The capacitive fluid sensor of claim 6, wherein said second insulating support member includes a central annular portion and plural arms extending from said central annular portion, said second insulating support member being fitted to a swollen-out portion of said sensor housing near said first housing end, said swollen-out portion increasin flow path area to reduce fluid flow resistance.

8. The capacitive fluid sensor of claim 7, wherein said plural arms are inclined away from said swollen-out portion of said sensor housing to provide easy insertion into said sensor housing, said plural arms being furthest apart near said first housing end.

9. The capacitive fluid sensor of claim 7, wherein said plural arms are inclined away from said swollen-out portion of said sensor housing to locate said internal electrode at a center of said sensor housing accurately, said plural arms being furthest apart near said second housing end.

10. The capacitive fluid sensor of claim 1, wherein said fluid includes a fuel mixture of gasoline and alcohol, and wherein a sensed dielectric constant represents a mixture ratio of gasoline and alcohol.

11. The capacitive fluid sensor of claim 1, wherein said capacitive fluid sensor inludes an oscillator circuit which generates a signal utilizing a capacitance sensed by said capacitive fluid sensor, said signal representing said capacitance as a frequency.

12. The capacitive fluid sensor of claim 1, wherein said outlet pipe is oriented at approximately a right angle with respect to said sensor housing.

* * * * *